(12) United States Patent
Anderson et al.

(10) Patent No.: US 12,178,566 B2
(45) Date of Patent: Dec. 31, 2024

(54) DETECTION AND MITIGATION OF INACCURATE SENSING BY AN IMPLANTED SENSOR OF A MEDICAL SYSTEM

(71) Applicant: Medtronic, Inc., Minneapolis, MN (US)

(72) Inventors: David A Anderson, Stanchfield, MN (US); James H Borowick, Minnetrista, MN (US); Hyun J. Yoon, Vadnais Heights, MN (US); Jon E. Thissen, Rosemount, MN (US); Shantanu Sarkar, Roseville, MN (US); Ashley L Galarneau, Minneapolis, MN (US); Jason C. Lee, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 940 days.

(21) Appl. No.: 17/101,945

(22) Filed: Nov. 23, 2020

(65) Prior Publication Data

US 2022/0160250 A1     May 26, 2022

(51) Int. Cl.
*A61B 5/06*     (2006.01)
*A61B 5/283*   (2021.01)
*A61B 5/339*   (2021.01)

(52) U.S. Cl.
CPC .............. *A61B 5/068* (2013.01); *A61B 5/065* (2013.01); *A61B 5/067* (2013.01); *A61B 5/283* (2021.01);
(Continued)

(58) Field of Classification Search
CPC ......... A61B 5/068; A61B 5/339; A61B 5/283; A61B 5/065; A61B 5/067; A61B 2562/0233; A61B 2562/0271
See application file for complete search history.

(56) References Cited

U.S. PATENT DOCUMENTS 5,803,915 A   9/1998  Kremenchugsky et al.
7,873,410 B2  1/2011  Cho et al.
(Continued)

FOREIGN PATENT DOCUMENTS

WO     2018122837     7/2018

OTHER PUBLICATIONS

International Search Report and Written Opinion of International Application No. PCT/US2021/052786, dated Feb. 3, 2022, 9 pp.

*Primary Examiner* — Linda C Dvorak
*Assistant Examiner* — Abigail Bock
(74) *Attorney, Agent, or Firm* — Shumaker & Sieffert, P.A.

(57) ABSTRACT

This disclosure is directed to techniques for detecting and mitigating inaccurate sensing in a medical system. In some examples, one or more sensors of the medical system may include at least one electrode configured to sense an impedance of a portion of a patient's body proximate to the electrode and processing circuitry of the medical system may detect an inaccuracy in the data corresponding to the one or more patient physiological parameters based upon data including at least the sensed impedance of the portion of the patient body; correct at least a portion of the inaccuracy in the data corresponding to the one or more patient physiological parameters; and generate, for display on a display device, output data indicating the inaccuracy in the data corresponding to the one or more patient physiological parameters.

12 Claims, 8 Drawing Sheets

(52) U.S. Cl.
CPC ...... *A61B 5/339* (2021.01); *A61B 2562/0233* (2013.01); *A61B 2562/0271* (2013.01)

(56) References Cited

U.S. PATENT DOCUMENTS

| | | |
|---|---|---|
| 9,101,281 B2 | 8/2015 | Reinert et al. |
| 9,205,263 B2 | 12/2015 | King et al. |
| 9,220,439 B2 | 12/2015 | Hauck |
| 9,282,895 B2 | 3/2016 | Wenzel et al. |
| 10,179,237 B2 | 1/2019 | Kane et al. |
| 10,426,955 B2 | 10/2019 | Sharma et al. |
| 10,448,856 B2 | 10/2019 | Weinberg et al. |
| 10,517,540 B1 * | 12/2019 | Anderson ................. A61B 5/30 |
| 10,660,579 B2 | 5/2020 | Narkiss et al. |
| 2011/0112442 A1 * | 5/2011 | Meger .................. A61B 5/4818 |
| | | 600/595 |
| 2013/0053714 A1 * | 2/2013 | Bornzin ............... A61N 1/3704 |
| | | 600/509 |
| 2020/0357519 A1 * | 11/2020 | Chakravarthy ........ A61B 5/316 |

* cited by examiner

DETECTION AND MITIGATION OF INACCURATE SENSING BY AN IMPLANTED SENSOR OF A MEDICAL SYSTEM

FIELD

The disclosure relates generally to medical systems and, more particularly, medical systems configured to monitor or detect health issues using one or more implanted sensors.

BACKGROUND

Medical systems often include one or more medical devices operative to monitor or detect health issues in a patient. Some types of medical devices may monitor a cardiac electrogram (EGM) of the patient to monitor the electrical activity of the patient's heart. A cardiac EGM is an electrical signal sensed via electrodes. In some examples, the medical devices monitor a cardiac EGM to detect one or more types of arrhythmia, such as bradycardia, tachycardia, fibrillation, or asystole (e.g., caused by sinus pause or AV block).

Some medical devices additionally or alternatively measure an impedance of the patient via a plurality of electrodes, e.g., to detect patient respiration, perfusion, or edema. Moreover, some medical devices additionally or alternatively include other sensors for sensing other physiological parameters of the patient. As examples, medical devices may include one or more sensors to sense patient posture and/or movement, temperature, heart sound, blood pressure, and oxygen saturation.

SUMMARY

An implantable medical device inserted into a specific portion of a patient's body is capable of making erroneous medical alerts if there is a problem with the medical device's ability to sense. Inaccurate sensing and other problems often correlate with one or more sensors being in an incorrect pose (e.g., position and/or orientation) either at the time of insertion or as a result of deviating (e.g., migrating and/or rotating) from a correct pose (e.g., position and/or orientation). Over time, it is possible for the patient's activities (e.g., normal and/or slight movements) to move (e.g., migrate) the medical device to a new position and/or rotate (e.g., flip) the medical device about an axis, causing the one or more sensors to be in the incorrect pose. An example sensor in an example incorrect pose may be designed to be inserted in a certain pose in order to interact with a particular tissue type (e.g., muscle) but, instead, is directed (e.g., flipped) towards an incompatible tissue type (e.g., fat). If the patient's body part of that particular tissue type is not proximate to the sensor, signals captured by the sensor may be distorted or corrupted.

In general, the disclosure is directed to techniques for detecting and mitigating inaccurate sensing by an implanted sensor of a medical system. Sensing in general by the implanted sensor may include sensing at least one patient physiological activity by capturing signals that vary based on the physiological activity. The medical system converts the captured signals into data corresponding to the at least one patient physiological activity but if the implanted sensor is not posed (e.g., positioned in the patient's body) as intended, the data generated by the medical system may be altered to extent that the some data be inaccurate. Some techniques employ various detection criteria specifying one or more thresholds for comparison with the (inaccurate) data corresponding to the at least one patient physiological activity. Multiple techniques may employ different detection criteria, for example, for different sensors, thresholds, formulas and/or the like. An example technique may employ detection criteria prescribing a formula for computing a detection score or index from the implanted sensor, and if that score or index exceeds a pre-determined threshold or otherwise satisfies a pre-determined criterion, the implanted sensor is flipped or rotated.

Correcting inaccuracies in the sensed data may be accomplished by executing a mitigation mechanism. Some techniques apply a mitigation mechanism configured to modify the captured signals, for example, by amplifying, reducing, or filtering a signal to change data carried by the signal. Other techniques apply a mitigation mechanism configured to modify medical condition tests applicable to the data corresponding to the at least one patient physiological activity.

In one example, a medical system comprises sensory sub-system comprising one or more sensors, each of the one or more sensors configured to capture a signal indicating one or more patient physiological parameters, the one or more sensors comprising at least one electrode configured to sense an impedance of a portion of the patient body proximate to the electrode; and sensing circuitry coupled to the one or more sensors and configured to generate data corresponding to the one or more patient physiological parameters; and processing circuitry configured to: detect an inaccuracy in the data corresponding to the one or more patient physiological parameters based upon data including at least the sensed impedance of the portion of the patient body; correct at least a portion of the inaccuracy in the data corresponding to the one or more patient physiological parameters; and generate, for display on a display device, output data indicating the inaccuracy in the data corresponding to the one or more patient physiological parameters.

In another example, a method of a medical system comprising: capturing, by one or more sensors of the medical system, at least one signal indicating one or more patient physiological parameters; sensing, by at least one electrode of the one or more sensors, an impedance of a portion of a patient body proximate to the at least one electrode; generating, by sensing circuitry coupled to the one or more sensors, data corresponding to the one or more patient physiological parameters; detecting, by processing circuitry of the medical system, an inaccuracy in the data corresponding to the one or more patient physiological parameters based upon data including at least the sensed impedance of the portion of the patient body; correcting, by the processing circuitry of the medical system, at least a portion of the inaccuracy in the data corresponding to the one or more patient physiological parameters; and generating, for display on a display device, output data indicating the inaccuracy in the data corresponding to the one or more patient physiological parameters.

In another example, a non-transitory computer-readable storage medium comprises program instructions that, when executed by processing circuitry of a medical system, cause the processing circuitry to capture, by one or more sensors of the medical system, at least one signal indicating one or more patient physiological parameters; sense, by at least one electrode of the one or more sensors, an impedance of a portion of a patient body proximate to the at least one electrode; generate, by sensing circuitry coupled to the one or more sensors, data corresponding to the one or more patient physiological parameters; detect, by the processing circuitry of the medical system, an inaccuracy in the data corresponding to the one or more patient physiological parameters based upon data including at least the sensed impedance of the portion of the patient body; correct, by the processing circuitry of the medical system, at least a portion of the inaccuracy in the data corresponding to the one or more patient physiological parameters; and generate, for display on a display device, output data indicating the inaccuracy in the data corresponding to the one or more patient physiological parameters.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

Figure 1:
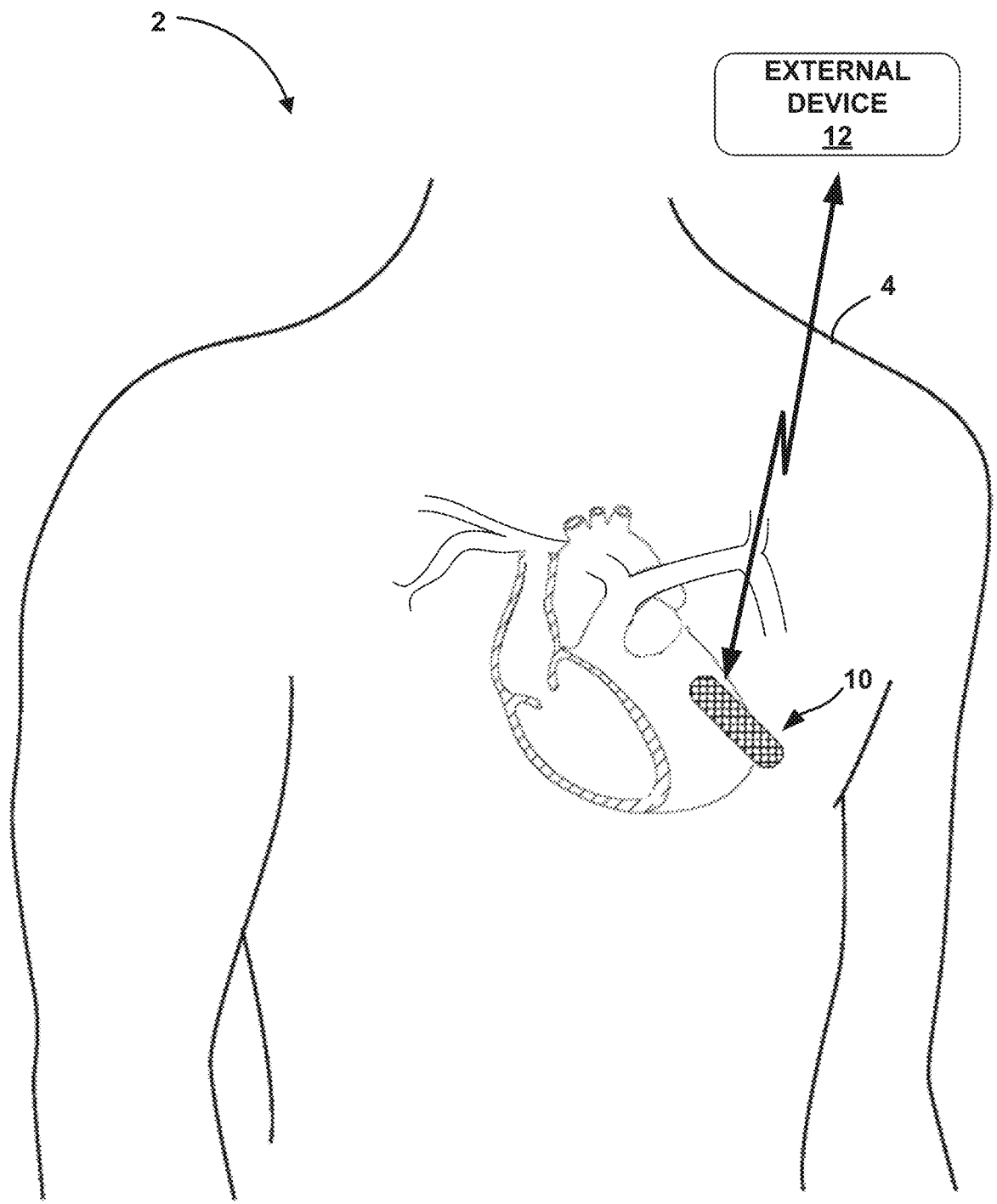
FIG. 1 illustrates the environment of an example medical system in conjunction with a patient.

In general, a device or combination of devices (e.g., in a system) may implement different types of hardware components of which various arrangements may be configured to execute different types of software components. Some devices execute the software component to operate internal mechanical components and control external devices. Medical devices as known to those skilled in a related art serve some health-related purpose. For a person who also is a patient of some type (e.g., a diabetes patient, a heart failure patient), a number of medical devices may improve a patient's health in terms of that patient's personal malady or maladies. Some medical devices employ sensing equipment to monitor aspects of the patient's physiology and in reliance of upon data generated during said monitoring, to detect occurrences of the patient's personal malady or maladies.

The sensing equipment employed by any medical device play a significant role in the proper operation of that medical device; however, under certain circumstances, the sensing may be unreliable, causing sensor data generated by the sensing equipment to be inaccurate. One example set of circumstances includes the medical device being in an unsuitable portion of the patient body or in an incorrect pose for accurate sensing. For example, when the medical device migrates and/or rotates and by doing so, becomes mispositioned, sensors of the sensing equipment may produce signals carrying inaccurate sensor data corresponding to the patient's physiological parameters.

When mispositioned, sensors such as an accelerometer, a bioimpedance sensor, an optical sensor, a temperature sensor, a signal strength meter, and/or the like may unexpectedly change signals or generate distorted signals e.g., given the effects of noise, such from electrical impedance, ambient light or temperature, or muscle activity. Cardiac EGMs may include noise, e.g., due to changing contact with tissue and/or orientation relative to heart. In some examples, flipped or migrated devices may correlate with a simultaneous changes or distortions in sensor data from multiple sensors (e.g. simultaneous change in impedance and accelerometer signals). When multiple independent sensors, which may have un-correlated trends, exhibit a distortion or change at a same time, it is very unlikely that two or more corresponding physiological parameters are changing at the same time; instead, device flipping/migration is more likely the cause of the simultaneous changes or distortions. The techniques described herein may be implemented with electrical activity (e.g., cardiac EGMs and impedance) sensed via subcutaneous electrodes, cutaneous electrodes, substernal electrodes, extravascular electrodes, intra-muscular electrodes, or any electrodes positioned in (or in contact with) any tissue of a patient.

A variety of types of medical devices sense cardiac EGMs and/or other physiological signals. Some medical devices that sense are non-invasive, e.g., using a plurality of electrodes or other sensors placed in contact with external portions of the patient, such as at various locations on the skin of the patient. The electrodes and/or other sensors in these non-invasive examples may be attached to the patient using an adhesive, strap, belt, or vest, as examples, and electrically coupled to a monitoring device, such as an electrocardiograph, Holter monitor, or other electronic device. The electrodes and/or other sensors may be configured to provide sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs and/or other physiological signals include wearable devices with electrodes and/or other sensors configured to contact the skin of the patient, such as patches, watches, or necklaces. One example of a wearable physiological monitor is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Implantable medical devices (IMDs) also sense and monitor cardiac EGMs and/or other physiological signals. The electrodes used by IMDs to sense cardiac EGMs are typically integrated with a housing of the IMD and/or coupled to the IMD via one or more elongated leads. Example IMDs that monitor cardiac EGMs and/or other physiological signals include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor, available from Medtronic plc, which may be inserted subcutaneously. Such IMDs may facilitate relatively longer-term monitoring of patients during normal daily activities, and may periodically transmit collected data to a network service, such as the Medtronic Carelink™ Network.

Regardless of which type or types of devices are used, a noise signal, which may be referred to as an artifact, may appear in a cardiac EGM provided by electrodes and/or other signals provided by the electrodes or other sensors. Such noise signals may be more prevalent when cutaneous, subcutaneous, or extravascular electrodes are used, e.g., due to temporary change in contact between at least one of the electrodes and the tissue where the electrode is located due to relative motion of the electrode and tissue. The presence of a noise signal in a sensed cardiac EGM, for example, may cause circuitry for detecting depolarizations, e.g., R-waves, to wrongly detect the noise signal as a depolarization. The noise signal may also cause the circuitry to then fail to sense a number of subsequent depolarizations because the noise signal may be much bigger in amplitude than the subsequent depolarizations and, in some cases, because the high-amplitude noise may cause an adjustable sensing threshold used by the circuitry to be adjusted to a level greater than the amplitude of the true depolarizations. Additionally, the amplitude of the cardiac signals, e.g., depolarizations, within the sensed cardiac EGM may vary over time, e.g., due to respiration. Such cardiac signal amplitude variation may also be more prevalent in cardiac EGMs sensed using cutaneous, subcutaneous, or extravascular electrodes. Variation in cardiac signal amplitude may also cause depolarizations to temporarily fall below a sensing threshold and, consequently, not be detected. These types of improper sensing of depolarizations may potentially trigger a false-positive indication of a cardiac event, such as asystole, that is not actually occurring in the patient.

Noise signals may be present in signals being produced by the other sensing equipment mentioned herein, e.g., an accelerometer, an optical sensor, a temperature sensor, and/or a bioimpedance. Devices may derive parameter values from signals generated by such sensors, but these values may be inaccurate e.g., due to the presence of the noise signals. Poor signal strength may also factor into any inaccuracy. As an operational requirement, some devices have to be proximate to a particular portion the patient's body, otherwise these devices do not operate properly. Non-compliance with this operational requirement, either at implantation or due to migrations/rotations post-implant, may cause (at least in part) the inaccurate sensing. In some examples, the inaccurate parameter values may be caused by the sensed impedance of a non-compliant proximate portion of the patient body. In other examples, some devices require one or more sensors to be positioned and/or oriented in a pre-determined pose but if these devices deviate from the pre-determined pose, the inaccurate parameter values may correlate with the deviated pose within the patient body. One example of a deviated pose is a "flipped device" which occurs when the medical device is rotated about an axis (e.g., a rotation of 180 degrees about a vertical or horizontal axis).

Medical systems according to this disclosure implement techniques for detecting and/or mitigating inaccurate sensing by a device by, for example, identifying an instance when the device is incorrectly positioned and/or oriented for sensing any of a patient's physiological parameters. In some examples, processing circuitry of a medical system analyzes data corresponding to sensed impedance to determine whether the data corresponding to one or more of the plurality of physiological parameters may be inaccurate (e.g., altered to an extent that the parameter data is inaccurate). Such an analysis may involve determining whether one or more detection criterion is satisfied. Examples of such detection criteria may be used to detect a "flipped device" and include sensor parameter thresholds or conditions, e.g., a sign change for accelerometer parameter values, an impedance at or near a maximum or minimum of bioimpedance parameter value depending on which way the device is flipped, a significant change in light based on optical sensor parameter values, and/or the like. An example accelerometer may measure changes in body posture assuming that the device is not moving or rotating or movements or rotations of the device with respect to a constant posture of the patient body and samples of the accelerometer parameter may provide these measurements as positional values for detecting when the device is flipped. The temperature parameter may be a value indicative of a relatively hotter portion of the patient body or a relatively colder portion of the patient body. The temperature parameter change depending on the orientation of the device (e.g., one side facing outside may be influenced more by ambient temperature or clothing). The bioimpedance sensor parameter provides values indicating a level of electrical impedance sensed by the device. The optical sensor parameter may determine whether the device is a certain position/orientation based on how much light is the optical sensor detects.

The techniques include detecting an inaccuracy in the data corresponding to the patient's physiological parameters based upon the sensed impedance of a proximate portion of the patient's body to the device. The device may be an insertable medical device with different electrodes and other sensors sampling measurements and other sensor data (e.g., continuously, periodically, or responsively) corresponding to the patient's physiological parameters. One use of the electrodes is to sense the impedance of tissue proximate to the device, which may vary significantly based on the type of tissue proximate to the electrodes. If the tissue proximate to the device is not compatible with accurate sensing by one or more of the medical device's sensors, the data corresponding to the patient's physiological parameters most likely is inaccurate.

The techniques allow the medical device to continue operation e.g., medical condition monitoring. In some examples, the medical device may proceed to detect medical, e.g., cardiac, events and conditions after successful mitigation of the inaccurate sensing. One example mechanism for mitigation is to adjust existing techniques (e.g., criteria) for monitoring/detecting medical conditions, for example, to account for noise in the sensor data corresponding to the physiological parameters. One example adjustment may include resetting baselines, thresholds, and/or parameters of detection algorithms for changes in the cardiac health/status/condition of the patient and other cardiac events, e.g., heart failure worsening or arrhythmia. Another example adjustment may be an adjustment to a component in a mathematical technique, such as a weight, an exponent, or a variable. Another mechanism modifies the electronic signals (e.g., electrogram signal data) generated by sensors, for example, by applying a signal processing technique to amplify, reduce, and/or filter the signals. Another technique adjusts the data corresponding to the physiological parameters to account for any distortion.

The processing circuitry may perform the techniques of this disclosure substantially in real-time in response to the detection of a medical condition, or during a later review of the data corresponding to the plurality of physiological parameters. In either case, the processing circuitry may include the processing circuitry of medical device that monitors a patient's physiological parameters for medical conditions and/or processing circuitry of another device, such as a local or remote computing device which retrieved the patient's physiological parameter data from the medical device. In this manner, the techniques of this disclosure may advantageously enable improved accuracy in the detection of medical conditions and, consequently, better evaluation of the condition of the patient. In this manner, the techniques of this disclosure may advantageously enable improved accuracy in the detection of changes in patient health and, consequently, better evaluation of the condition of the patient.

FIG. 1 illustrates the environment of an example medical system 2 in conjunction with a patient 4, in accordance with one or more techniques of this disclosure. The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1), and is configured to sense a cardiac EGM via the plurality of electrodes. In some examples, IMD 10 takes the form of the LINQ™ ICM available from Medtronic, Inc. of Minneapolis, MN IMD 10 includes one or more sensors configured to sense patient activity, e.g., one or more accelerometers.

External device 12 may be a computing device with a display viewable by the user and an interface for receiving user input to external device 12. In some examples, external device 12 may be a notebook computer, tablet computer, workstation, one or more servers, cellular phone, personal digital assistant, or another computing device that may run an application that enables the computing device to interact with IMD 10.

External device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., radiofrequency (RF) telemetry according to the 802.11 or Bluetooth® specification sets, or other communication technologies operable at ranges greater than near-field communication technologies).

External device 12 may be used to configure operational parameters for IMP 10. External device 12 may be used to retrieve data from ID 10. The retrieved data may include data (e.g., values) corresponding to patient physiological parameters measured by IMD 10, indications of episodes of arrhythmia or other maladies detected by IMD 10, and physiological signals recorded by IMD 10. For example, external device 12 may retrieve data recorded by ID 10 capturing the physiological signals and other electrical signals via one or more sensors (e.g., an optical sensor, a temperature sensor, an accelerometer, and/or the like). The one or more sensors operated by IMD 10 may, based on the captured signals, sense impedance, cardiac electrical activity, position/movement, light, temperature, and other patient physiological parameters. As an example, external device 12 may retrieve cardiac EGM segments recorded by IMD 10 due to IMD 10 determining that an episode of asystole or another malady occurred during the segment. As another example, external device 12 may receive data corresponding to a sensed impedance of a portion of the patient body proximate to an electrode, indications of detected inaccuracies in data corresponding to one or more patient physiological parameters, indications that the one or more sensors are inappropriately positioned and/or oriented in the patient body, determinations that the detected inaccuracies correlate to an inappropriate pose in the patient body, corrections for the detected inaccuracies in data corresponding to one or more patient physiological parameters, or other data related to the techniques described herein from IMP 10. As will be discussed in greater detail below with respect to FIG. 5, one or more remote computing devices may interact with IMP 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques for detecting and/or mitigating instances of inaccurate sensing of medical system 2, e.g., of IMP 10, external device 12, and/or any other computing device of this disclosure. Processing circuitry 50 (FIG. 2) of IMP 10 may be communicably coupled to one or more sensors, each being configured to sense at least one patient physiological parameters in some form, and sensing circuitry configured to generate (sensor) data corresponding to the at least one patient physiological parameters. To determine whether there is any inaccuracy in the data corresponding to the at least one patient physiological parameters, processing circuitry 50 of IMD 10, processing circuitry 80 (FIG. 4) of external device 12 and/or processing circuitry of one or more other devices, such as processing circuitry 98 of server 94 (FIG. 5), may access data generated from captured electrical signals including data corresponding to the sensed impedance of the portion of the patient body and apply an algorithm to determine whether such data indicates inaccurate sensing of patient physiological parameters (e.g., due to an inappropriate pose of IMD 10 within patient body). To correct the inaccuracy in the data, the processing circuitry may modify the data corresponding to the one or more patient physiological parameters and/or the captured signals (e.g., physiological signals) from the one or more sensors, for example, by adjusting sensor data derived from the captured signals, by applying a signal processing algorithm to modify the captured signals and from the modified signals, derive modified data corresponding to the one or more patient physiological parameters.

In some examples, the processing circuitry is further configured to detect, based upon the sensed impedance of the portion of the patient body, that the portion of the patient body differs from a pre-determined portion of the patient body where the pre-determined portion was previously identified as an implantation site for IMD 10. In addition to the implantation site for IMD 10, the processing circuitry may specify a pre-determined pose (e.g., posture) of the one or more sensors within the patient; and if, based upon the data corresponding to the one or more patient physiological parameters including the sensed impedance of the portion of the patient body, a pose (e.g., an actual pose) of the one or more sensors within the patient body differs from the pre-determined pose within the patient body processing circuitry 50 may determine that the inaccuracy correlates with the (actual) pose within the patient body. In some examples, the processing circuitry may define differences between the actual pose and the pre-determined pose, for instance, as deviations in terms of position and/or orientation changes (e.g., a migration and/or a rotation) within the patient body.

In some examples, processing circuitry of medical system 2 may detect an inaccuracy correlating with a simultaneous/cotemporaneous change in the respective sensor data captured by each of multiple sensors (e.g. a simultaneous change in impedance and accelerometer signals). When multiple independent sensors, which may have un-correlated trends, exhibit changes in signals at a same time, it is very unlikely that two or more corresponding physiological parameters are changing at the same time; instead, the migration and/or rotation of the multiple sensors within the patient body more likely the cause of the simultaneous changes.

Processing circuitry of medical system 2 may employ various detection criteria to determine whether any portion of the data corresponding to the one or more patient physiological parameters is inaccurate, for example, due (at least in part) to IMD 10 being migrated and/or rotated. In some examples, the processing circuitry may compare the data corresponding to the one or more physiological parameters with respective detection criteria for at least one of a migration or a rotation of the one or more sensors in IMD 10; and based upon the comparison, compute a detection score for determining whether the one or more sensors had the at least one of the migration of the rotation. An example detection criterion may specify a weight for parameter value used in computing the detection score and another detection criterion may specify a threshold for determining whether the detection score satisfies the detection criteria. In some examples, based on satisfaction of the detection criteria, the processing circuitry may determine that an occurrence of the at least one of the migration or the rotation has likely occurred.

Processing circuitry of medical system 2 may employ at least one mitigation mechanism in response to a likely occurrence of the at least one of the migration of the rotation. In some examples, the processing circuitry may communicate the detection score as a confidence level for a medical condition alert for the patient, or communicate a confidence level determined based on the detection score. Because IMD 10 may be generally configured to monitor cardiac activity and if the patient's heart needs attention due to some medical condition, to output some type of an alert, providing the confidence level to accompany the alert may be advantageous to the patient or the patient's caregiver. If the detection score indicates IMD 10 most likely migrated and/or rotated to an extent that results in the detected inaccuracy, the patient or the patient's caregiver may choose to disregard the medical condition alert as a false determination, in effect rejecting the medical condition (e.g., heart failure) predicted or detected for the patient by IMD 10. To illustrate another benefit to the patient or the patient's caregiver based upon the detection score, if the detection score is determined to fall below a certain minimum or exceed a certain maximum, the processing circuitry may reject the medical condition prediction and withhold the medical condition alert from output, preventing display on a display device of the medical condition alert.

Processing circuitry of medical system 2 may employ one or more mitigation mechanisms for fine-tuning one or more criterion for detecting any inaccuracy in the data corresponding to the at least one patient physiological parameter. As one example mechanism, the processing circuitry may be configured to modify one or more of the respective detection criteria for the at least one of a migration or a rotation of the one or more sensors. By doing so, medical system 2 may improve upon sensitivity and/or specificity of the detection of a flipped or migrated IMD by reducing false positives or false negatives. Processing circuitry 50 of IMD 10 may modify a detection criterion for only that IMD 10 or (via external device 12 or a networked system, e.g., as described with respect to FIG. 5) distribute the modified detection criterion for other patient's IMDs 10. One example mechanism may modify the one or more criterion periodically or responsively, e.g., in response to IMD 10 receiving a user command. The processing circuitry may modify a first detection criterion and a second detection criterion: The first detection criterion may specify, for the comparison, a factor or an operative feature of the at least one of a migration or a rotation to detect which amongst parameter values and the second detection criterion specifies a condition or a threshold value for the comparison with the parameter value, the partial detection score, or the detection score. The processing circuitry may modify a metric used in computing parameter values including any scale/instrumentation used in sensor measurements, any function/logic used in deriving a parameter value from the sensor measurements, or any detection scoring process/formula. With respect to examples of detection scoring, the processing circuitry may aggregate multiple parameter values into a multi-variate function for computing a detection score; to improve upon that function's accuracy at detecting the at least one of a migration or a rotation of the one or more sensors, the processing circuitry may modify any component (e.g., weight, coefficient, exponent, and/or the like) therein.

Processing circuitry of medical system 2 may correct at least a portion of the inaccuracy in the data corresponding to the one or more patient physiological parameters and then, generate, for display on a display device, output data identifying the inaccuracy in the data corresponding to the one or more patient physiological parameters. Processing circuitry of medical system 2, e.g., processing circuitry 50 of IMD 10, may invalidate the data corresponding to the one or more patient physiological parameters if at least one attempt at correction is unsuccessful at correcting the at least a portion of the inaccuracy in the data corresponding to the one or more patient physiological parameters. Although described in the context of examples in which IMD 10 comprises an insertable cardiac monitor, example systems including one or more implantable, wearable, or external devices of any type configured to sense patient physiological parameters (e.g., a cardiac EGM) may be configured to implement the techniques of this disclosure.

In some examples, processing circuitry in a wearable device may execute same or similar logic as the logic executed by processing circuitry of IMD 10 and/or other processing circuitry as described herein. In this manner, a wearable device or other device may perform some or all of the techniques described herein in the same manner described herein with respect to IMD 10. In some examples, the wearable device operates with IMD 10 and/or external device 12 as potential providers of computing/storage resources and sensors for monitoring patient activity and other patient parameters. For example, the wearable device may communicate the patient activity data to external device 12 for storage in non-volatile memory and for computing daily activity metric values from peak patient activity data and non-peak patient activity data. Similar to processing circuitry of IMD 10, processing circuitry of external device 12 may analyze the patient activity data to determine which peak and non-peak periods to use in computing the daily activity metric values.

Figure 2:
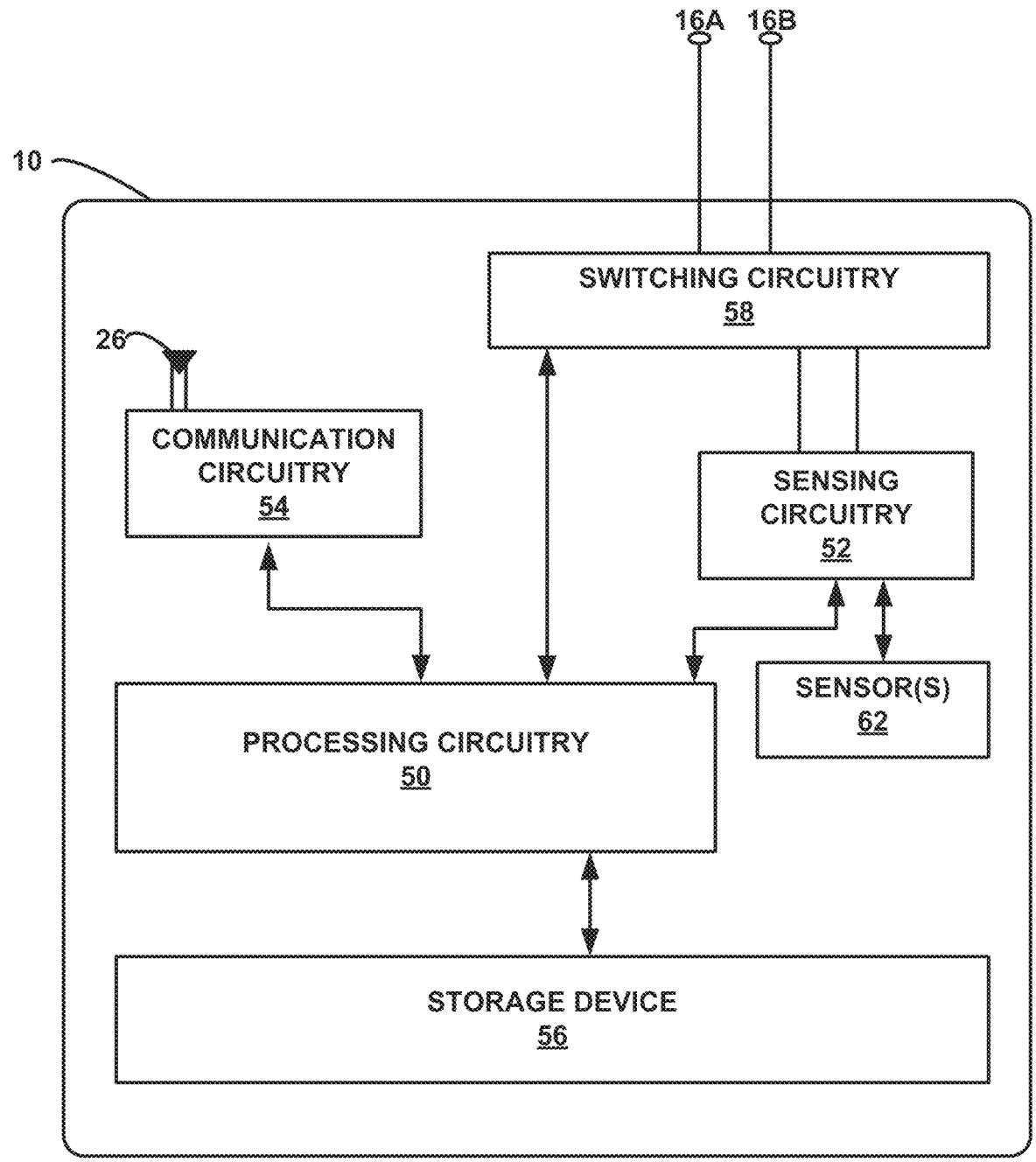
FIG. 2 is a functional block diagram illustrating an example configuration of the implantable medical device (IMD) of the medical system of FIG. 1.

FIG. 2 is a functional block diagram illustrating an example configuration of IMD 10 of FIG. 1 in accordance with one or more techniques described herein. In the illustrated example, IMD 10 includes electrodes 16A and 16B (collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to sense electrical signals of the heart of patient 4, for example by selecting electrodes 16 and polarity, referred to as the sensing vector, used to sense a cardiac EGM, as controlled by processing circuitry 50. Sensing circuitry 52 may monitor and sense signals from electrodes 16, e.g., to produce a cardiac EGM, in order to facilitate monitoring the electrical activity of the heart. Sensing circuitry 52 may also deliver signals via electrodes 16 to generate data corresponding to an electrical impedance proximate to electrodes 16. Sensing circuitry 52 may monitor and sense signals from sensors 62, which may include one or more accelerometers, temperature sensors, pressure sensors, optical sensors, and/or signal strength meters as examples.

The signals received from sensor(s) 62 encode a plurality of patient physiological parameters. In some examples, sensing circuitry 52 may apply a signal processing technique to modify the signals from electrodes 16 and sensors 62 (e.g., downsampling, upsampling, filtering, and/or the like). In some examples, sensing circuitry 52 may include one or more filters and amplifiers for filtering and amplifying signals received from electrodes 16 and/or sensors 62. Sensing circuitry 52 may capture signals from any one of sensors 62, e.g., to produce (sensor) data corresponding to one or more patient physiological parameters, in order to facilitate monitoring of patient 4 (e.g., for certain medical conditions such as an arrhythmia) and detecting changes in patient health. Sensing circuitry 52 and processing circuitry 50 may store the sensor data in storage device 56.

Sensing circuitry 52 may be configured to determine an electrical impedance present in the signals from electrodes 16, e.g., to identify patient body portions (e.g., muscle tissue, bone, and/or another body part) in proximity to IMD 10. In some examples, there may be differences between human muscle tissue and bone with respect to how each may affect the electrical impedance observed by sensing circuitry 52 via electrodes 16. If those effects are consistent across a patient group or population, the present disclosure describes a number of benefits to patient 4 that are now possible by medical system 2 leveraging those differences. Processing circuitry 50 of IMD 10 may measure the electrical impedance proximate to electrodes 16 and, as one advantageous use of that measurement, determine whether IMD 10—or, specifically, one or more of electrodes 16—are in an unsuitable position where IMD 10 cannot properly measure sensor data and/or otherwise operate as configured.

Sensing equipment such as electrodes 16 and sensors 62 may be located on or directed to a particular "side" of IMD 10, which may be intended for insertion in a particular position and orientation within the patient's body. When inserted into patient 4, medical professionals select an appropriate implantation site for IMD 10 as a suitable patient body portion for the sensing equipment to sense a plurality of physiological parameters. IMD 10 (and insertable medical devices in general) may rotate and/or migrate away from that implantation site, causing electrodes 16 and/or sensors 62 to distort any data corresponding to the sensed physiological parameters. When insertable medical devices in general move away from their proper implantation site, surgery may be needed to reposition those devices. To mitigate such an impropriety without surgery, processing circuitry of medical system 2 may correct the data generated by these insertable medical devices.

IMD 10 may configure one or more of electrodes 16 to sense electrical activity (including impedance) when proximate to a muscle tissue section, but if IMD 10 happens to rotate and/or migrate, the one or more of electrodes 16 may become proximate to a fatty tissue section of patient 4 despite being suited for muscle tissue and vice versa. In other examples, IMD 10 may rotate and/or migrate such that the one or more of electrodes 16 become proximate to bone, which provides little or no useful data corresponding to the sensed electrical activity. Similarly, if IMD 10 rotates and/or migrates, one or more of sensors 62 may become proximate to the fatty tissue even though the one or more of sensors 62 may be suitable for sensing respective physiological parameters when proximate to the muscle tissue section of patient 4.

Processing circuitry 50, executing logic configured to perform a detection analysis on the sensor data, is operative to detect instances of inaccurate sensing by IMD 10. Processing circuitry 50 and sensing circuitry 52 may control one or more of sensors 62 to sense patient physiological data in parameterized form: patient activity counts based upon data from an accelerometer (e.g., a three-axis accelerometer), pose data based upon data from a gyroscope, moment data from a transducer, and/or the like. The actual position and orientation of IMD 10 may distort signals generated by sensors 62, negatively affecting accuracy of the parameterized patient physiological data. Normal movements of patient 4 may cause any insertable device to migrate or rotate to another portion (of patient 4) and if that portion of patient 4 is not suitable for accurately sensing the parameterized patient physiological data, processing circuitry 50 of IMD 10 (and/or other processing circuitry of the medical device system) relies upon the executing logic to detect the unsuitable portion and then, attempt to mitigate any resulting inaccuracy in the parameterized patient physiological data.

Processing circuitry 50 of IMD 10, while under the control of the executed logic programmed with the above example detection analysis, may apply one or more detection criterion to data corresponding to certain physiological parameters and computes a detection score indicative of a likelihood that IMD 10 is in an unsuitable portion of patient 4's body and/or is in an inappropriate pose for accurately sensing patient 4's physiological data from signals generated by sensors 62. Processing circuitry 50 of IMD 10 may apply a mechanism specified by the detection criteria to compute the detection score. One mechanism may specify a probability distribution and a set of respective conditional probabilities for the certain physiological parameters while another mechanism may specific a mathematical function and a set of respective weights for the certain physiological parameters. Another example detection criterion specifies a threshold for comparing with the detection score and determining whether IMD 10 is or is not accurately sensing the certain physiological parameters.

Although the present disclosure describes techniques performed by processing circuitry 50 of IMD 10, for instance, to track the certain physiological parameters over time and detect an occurrence of inaccurate sensing and/or a mispositioned IMD 10, any insertable or otherwise implantable medical device with different sensors continuously measuring various aspects of patient physiological activity may be perform the detection analysis and determine whether such a medical device is operating properly or is mispositioned within patient 4. Any insertable medical device having processing circuitry may execute same or similar logic for the detection analysis executed in processing circuitry 50 of IMD 10 and/or processing circuitry 80 of external device 12. Similar to IMD 10 migrating and/or rotating to a portion of patient 4 unsuitable for accurate sensing, these insertable or implantable medical devices may migrate and/or rotate away from an implantation site and end up in a position and/or orientation negatively affecting their operation. In some examples, an electrical impedance affecting circuitry of an insertable medical device is sufficient to distort data generated by that device. One use of electrodes such as electrodes 16 is to sense the impedance associated with the tissue proximate to the device/electrodes, which may vary significantly based on the type of tissue proximate to the electrodes. In addition, these insertable medical devices may apply a mechanism for mitigating their improper operation due to being mispositioned in patient 4 (without repositioning), for example, by communicating a confidence level for that device and correcting the distorted data.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth, WiFi, or other proprietary or non-proprietary wireless communication schemes.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include data corresponding to the plurality of patient physiological parameters including data corresponding to electrical activity in patient 4 such as the sensed impedance, episode data such as a cardiac EGM depicting suspected changes in cardiac activity, and/or indications of changes in patient health including indications of satisfaction of any one of various medical condition prediction criteria.

Figure 3:
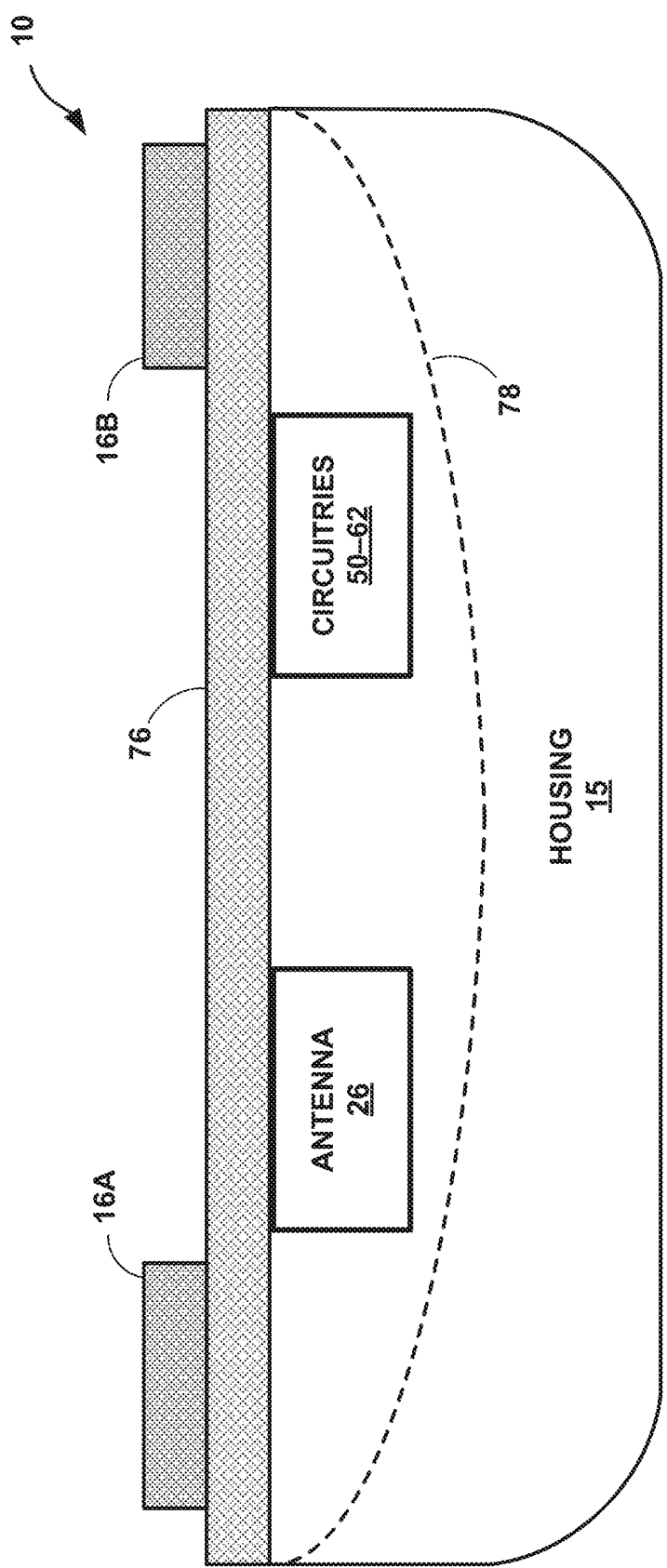
FIG. 3 is a conceptual side-view diagram illustrating an example configuration of the IMD of FIGS. 1 and 2.

FIG. 3 is a conceptual side-view diagram illustrating an example configuration of IMD 10 of FIGS. 1 and 2. While different examples of IMD 10 may include leads, in the example shown in FIG. 3, IMD 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
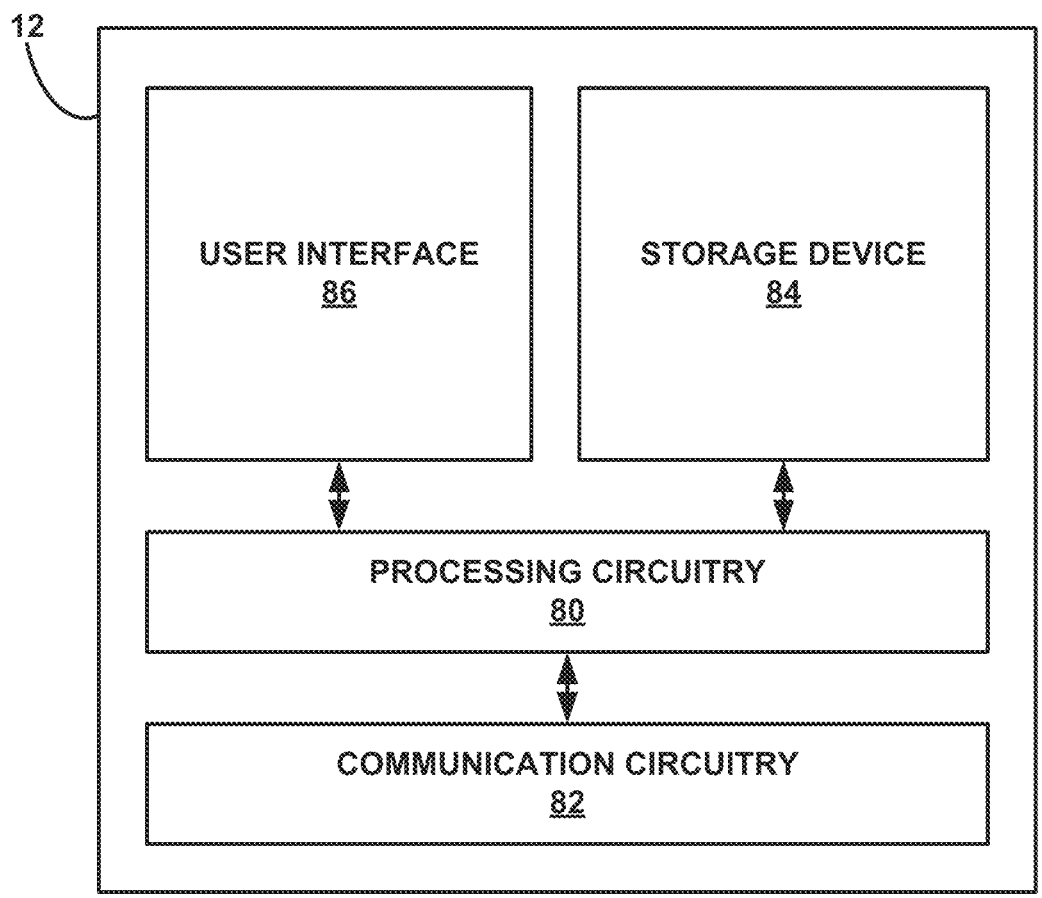
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, NFC, RF communication, Bluetooth, WiFi, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data informative of detected medical conditions, such as arrhythmia episode data that may include cardiac EGMs), data indicative of sensed impedance, and data corresponding to a plurality of patient physiological parameters) to external device 12. In turn, external device 12 may receive the collected data from IMD 10 and store the collected data in storage device 84. The data external device 12 receives from IMD 10 may include a confidence level to accompany the detected medical condition (e.g., the arrhythmia episode data), corrected episode data from modified signals, corrected physiological parameter data, indications of inaccurate sensing, and/or indications of an inappropriate pose for ID 10. Processing circuitry 80 may implement any of the techniques described herein to analyze data from IMD 10, e.g., to determine whether IMD 10 is inaccurately sensing the physiological parameters, which may be due to being migrated and/or rotated to an unsuitable position for accurately sensing the physiological parameters of patient 4. As discussed herein, the physiological parameters may be used to determine whether the patient is experiencing a change in health e.g., based upon one or more prediction criterion. In some examples, processing circuitry 80 of external device 12 may perform some or all of the techniques, described herein primarily with respect to processing circuitry 50 of IMD 10, for determining identifying sensing inaccuracy in data received from IMD 10 and determining whether a pose of IMD 10 has likely changed, and for mitigating such inaccuracies.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., patient physiological parameters, indications of changes in the patient physiological parameters, and indications of changes in patient health that correlate to the changes in the patient physiological parameters, determinations of probability data of possible medical conditions to predict, detections of inaccurate sensing of the patient physiological parameters, detections of migration(s) and/or rotation(s) of IMD 10 based upon sensed electrical activity in patient 4, determinations of correlations between the inaccurate sensing and the migration(s) and/or rotation(s) of IMD 10, metric values, sensed electrical activity including sensed impedance, episode data, cardiac EGM, ECG, electrocardiogram, cardiac electrogram, and/or the like. In addition, user interface 86 may include an input mechanism configured to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Figure 5:
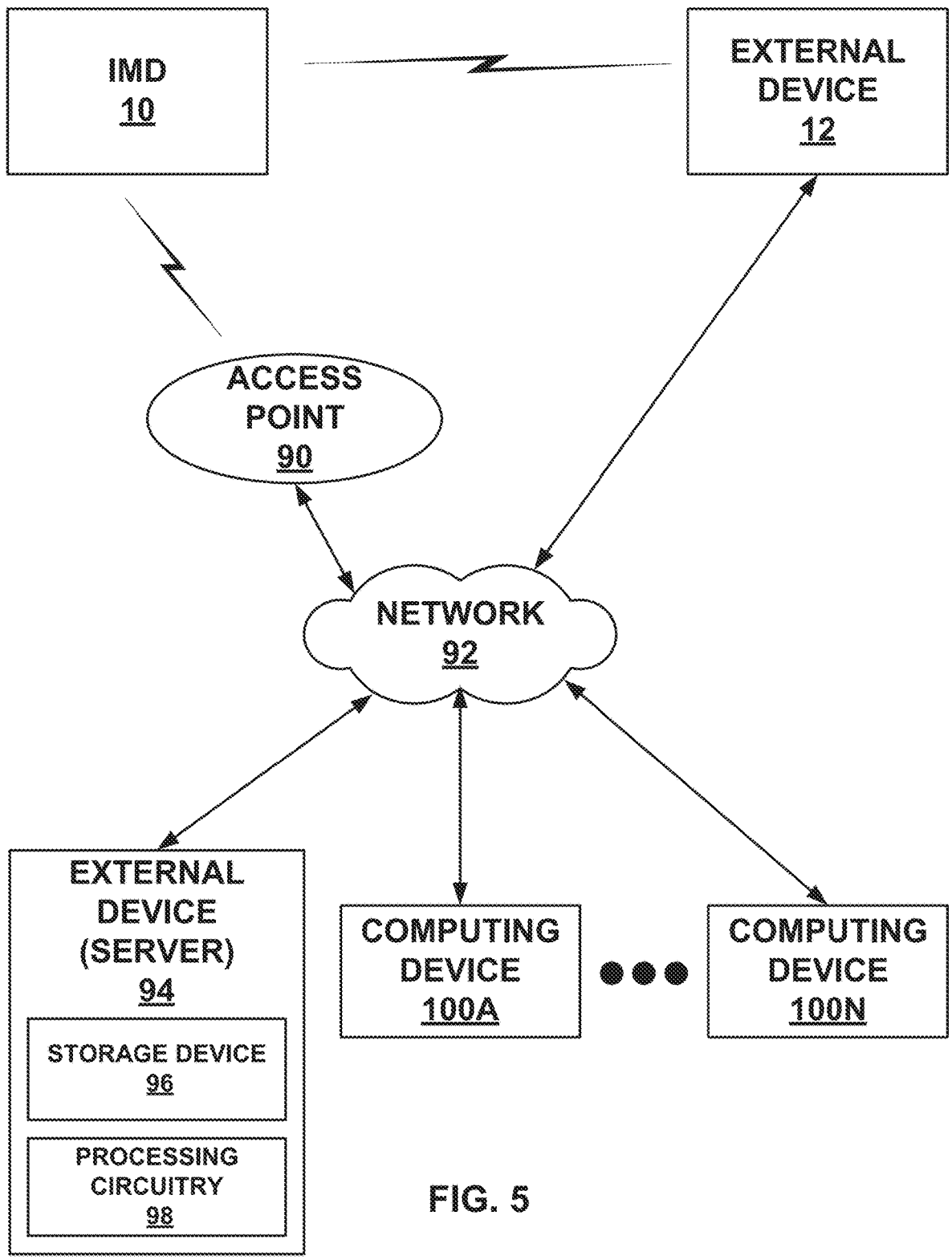
FIG. 5 is a block diagram illustrating an example system that includes an access point, a network, external computing devices, such as a server, and one or more other computing devices, which may be coupled to the IMD and external device of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as patient 4's physiological parameters including sensor data and electrical activity data, indications of inaccurate sensing of one or more of patient 4's physiological parameters, indications of migrations and/or rotations to an unsuitable portion of patient 4, electrograms and other physiological parameter data, and/or indications of changes in patient health, to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, one or more of computing devices 100 may be a tablet or other smart device located with a clinician, by which the clinician may program, receive alerts from, and/or interrogate IMD 10. For example, the clinician may access data corresponding to patient 4's physiological parameters including sensor data and electrical activity data, indications of inaccurate sensing of one or more of patient 4's physiological parameters, indications of migrations and/or rotations to an unsuitable portion of patient 4, metric values, episode data, electro cardiogram, and/or indications and/or indications of patient health collected by IMD 10 through a computing device 100, such as when patient 4 is in in between clinician visits, to check on a status of a medical condition. In some examples, the clinician may enter instructions for a medical intervention for patient 4 into an application executed by computing device 100, such as based on a status of a patient condition determined by IMD 10, external device 12, server 94, or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze information, data, or data received from IMD 10, e.g., to determine whether a health status of patient 4 has changed, to determine whether a confidence level of any changed health status determination indicates a false or a true determination, to determine whether a portion of patient 4 proximate to IMD 10 is suitable for sensing physiological parameters for the determination whether the health status of patient 4 has changed, to determine whether detection criteria for migration(s) and/or rotation(s) of IMD 10 are satisfied, and to determine whether the migration(s) and/or rotation(s) of IMD 10 correlate with the false determination of the changed health status of patient 4.

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
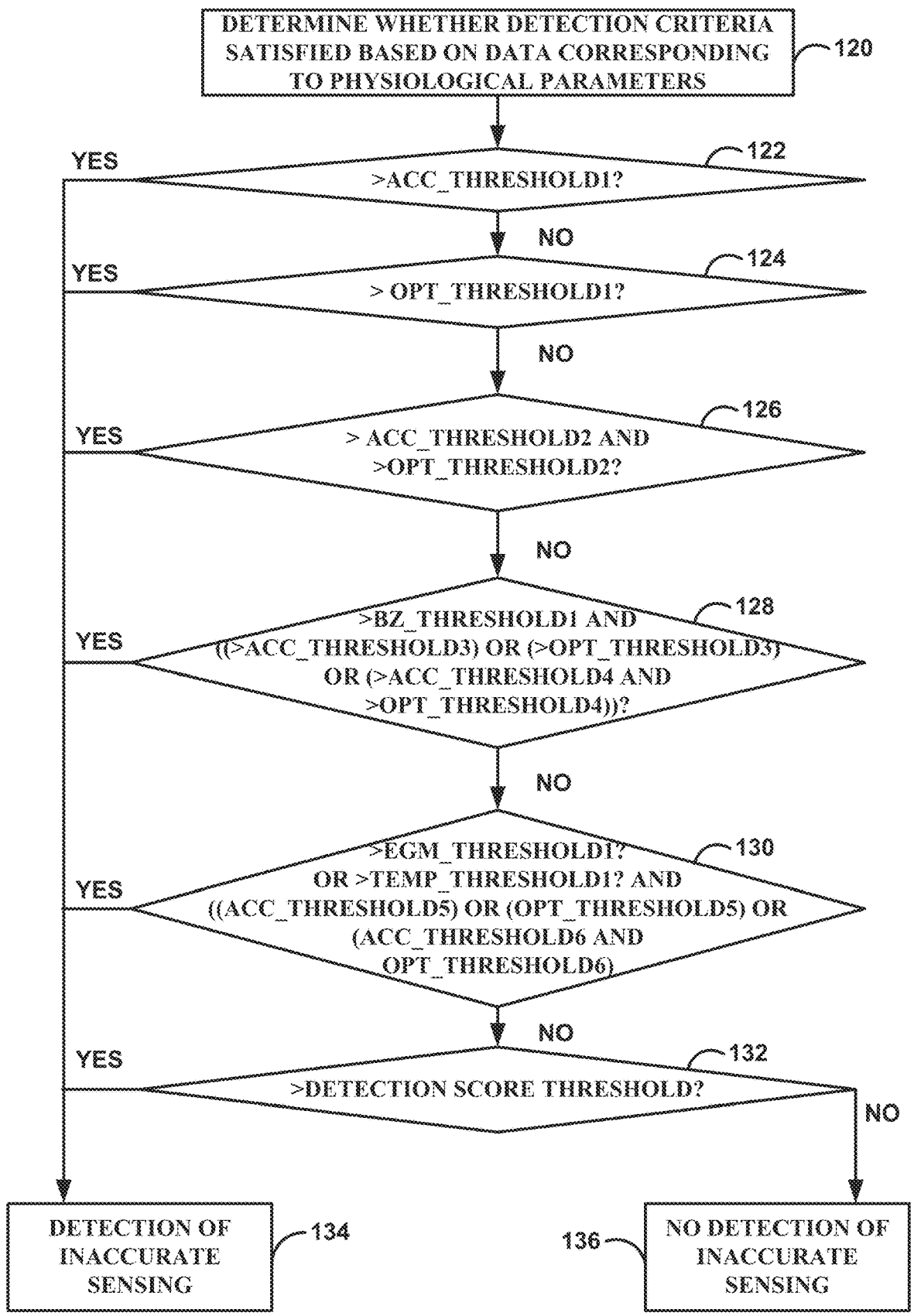
FIG. 6 is a flow diagram illustrating an example operation for detecting inaccurate sensing of patient physiological activity.

FIG. 6 is a flow diagram illustrating an example operation for detecting inaccurate sensing by an insertable medical device. According to the illustrated example of FIG. 6, processing circuitry of a medical system (e.g., processing circuitry of medical system 2 such as processing circuitry 50 of IMD 10) determines that at least one detection criterion is satisfied based on data generated by sensing circuitry (e.g., sensing circuitry 52 of IMD 10) including data corresponding to physiological parameters of patient 4 (120). For example, as discussed in greater detail with respect to FIG. 2, processing circuitry 50 may determine whether a parameter value satisfies a corresponding parameter threshold specified in the at least one detection criterion. As another example, processing circuitry 50 may compute a detection score from data corresponding to one or more patient physiological parameters and determine whether that detection score satisfies a corresponding detection score threshold specified in the at least one detection criterion.

Processing circuitry of the insertable medical device determines whether a first accelerometer parameter value satisfies (e.g., is greater than) a first accelerometer parameter threshold (value) (122). In FIG. 6, "ACC_THRESHOLD1" represents the first accelerometer parameter threshold. Based on determining that the first accelerometer parameter threshold is satisfied (YES of 122), the processing circuitry of the insertable medical device proceeds to output data indicating a detection of inaccurate sensing (134).

Based on determining that the first accelerometer parameter threshold is not satisfied (NO of 122), the processing circuitry of the insertable medical device determines whether a first optical sensor parameter value satisfies (e.g., is greater than) a first optical sensor parameter threshold (value) (124). In FIG. 6, "OPT_THRESHOLD1" represents the first optical sensor parameter threshold. Based on determining that the first optical sensor parameter threshold is satisfied (YES of 124), the processing circuitry of the insertable medical device proceeds to output data indicating a detection of inaccurate sensing (134).

Based on determining that the first optical sensor parameter threshold is not satisfied (NO of 124), the processing circuitry of the insertable medical device determines whether a second accelerometer parameter value and a second optical sensor parameter value satisfy (e.g., is greater than) a second accelerometer parameter threshold and a second optical sensor parameter threshold, respectively (126). In FIG. 6, "ACC_THRESHOLD2" and "OPT_THRESHOLD2" represents the second accelerometer parameter threshold and the second optical sensor parameter threshold, respectively. Based on determining that the second accelerometer parameter threshold and the second optical sensor parameter threshold are satisfied (YES of 126), the processing circuitry of the insertable medical device proceeds to output data indicating a detection of inaccurate sensing (134).

Based on determining that the second accelerometer parameter threshold and the second optical sensor parameter threshold are not satisfied (NO of 126), the processing circuitry of the insertable medical device determines whether a first bioimpedance parameter value satisfies a first bioimpedance parameter threshold and at least one of a third accelerometer parameter value satisfies a third accelerometer parameter threshold, or a third optical sensor parameter value satisfies a third optical sensor parameter threshold, or both a fourth accelerometer parameter value satisfies a fourth accelerometer parameter threshold and a fourth optical sensor parameter value satisfies a fourth optical sensor parameter threshold (128). In FIG. 6, "BZ_THRESHOLD1", "ACC_THRESHOLD3", "ACC_THRESHOLD4", "OPT_THRESHOLD3", and "OPT_THRESHOLD4" represent the first bioimpedance parameter threshold, the third accelerometer parameter threshold, the fourth accelerometer parameter threshold, the third optical sensor parameter threshold, and the fourth optical sensor parameter threshold, respectively. Based on determining that the first bioimpedance parameter threshold and at least one of the third accelerometer parameter threshold, the third optical sensor parameter threshold, or both the fourth accelerometer parameter threshold and the fourth optical sensor parameter threshold are satisfied (YES of 128), the processing circuitry of the insertable medical device proceeds to output data indicating a detection of inaccurate sensing (134).

Based on determining that the first bioimpedance threshold and at least one of the third accelerometer parameter threshold, the third optical sensor parameter threshold, or both the fourth accelerometer parameter threshold and the fourth optical sensor parameter threshold are not satisfied (NO of 128), the processing circuitry of the insertable medical device determines whether at least one of a first electrogram parameter value satisfies a first electrogram parameter threshold or a first temperature parameter value satisfies a first temperature parameter threshold and whether at least one of a fifth accelerometer parameter value satisfies a fifth accelerometer parameter threshold, or a fifth optical sensor parameter value satisfies a fifth optical sensor parameter threshold, or both a sixth accelerometer parameter value satisfies a sixth accelerometer parameter threshold and a sixth optical sensor parameter value satisfies a sixth optical sensor parameter threshold (130). In FIG. 6, "EGM_THRESHOLD1", "TEMP_THRESHOLD1", "ACC_THRESHOLD5", "ACC_THRESHOLD6", "OPT_THRESHOLD5", and "OPT_THRESHOLD6" represent the first electrogram parameter threshold, the first temperature parameter threshold, the fifth accelerometer parameter threshold, the sixth accelerometer parameter threshold, the fifth optical sensor parameter threshold, and the sixth optical sensor parameter threshold, respectively. Based on determining that at least one of the first electrogram parameter threshold or the first temperature parameter threshold and that at least one of the fifth accelerometer parameter threshold, the fifth optical sensor parameter threshold, or both the sixth accelerometer parameter threshold and the sixth optical sensor parameter threshold are satisfied (YES of 130), the processing circuitry of the insertable medical device proceeds to output data indicating a detection of inaccurate sensing (134).

Based on determining that at least one of the first electrogram parameter threshold or the first temperature parameter threshold and that at least one of the fifth accelerometer parameter threshold, the fifth optical sensor parameter threshold, or both the sixth accelerometer parameter threshold and the sixth optical sensor parameter threshold are not satisfied (NO of 130), the processing circuitry of the insertable medical device determines whether a detection score satisfies a detection score threshold (132). Based on determining that the detection score threshold is satisfied (YES of 132), the processing circuitry of the insertable medical device proceeds to output data indicating a detection of inaccurate sensing (134).

Based on determining that the detection score threshold is not satisfied (NO of 132), the processing circuitry of the insertable medical device proceeds to output data indicating no detection of inaccurate sensing (136). In some examples, the processing circuitry does not output any data indicating no detection of inaccurate sensing and continues normal operation. In other examples, based on determining that the at least one detection criterion is not satisfied, the example operation of FIG. 6 ends.

Based on determining that the at least one detection criterion is satisfied, the processing circuitry of the insertable medical device determines whether to apply a mechanism to mitigate the inaccurate sensing. In some examples, the processing circuitry may determine whether the satisfaction of the at least one detection criterion sufficiently indicates that the medical device is in mispositioned or in an incorrect pose prior to applying the mitigation mechanism. As one example mechanism, the processing circuitry of the insertable medical device may modify signals captured from sensors, for example, by enlarging and/or shortening the signals to overcome the effects from electrical impedance. The processing circuitry may apply a signal processing algorithm to effectuate such modification and by doing so, the processing circuitry may revert the signals back to an undistorted form such that any parameter value derived from these signals is no longer inaccurate.

As another example mechanism, the processing circuitry of the insertable medical device may modify the at least one detection criterion, for example, by modifying one or more parameter thresholds and/or the detection score threshold. In some examples, the processing circuitry may modify a multi-variate function used to compute the detection score, for example, by coefficients, weights, exponents, and/or other components of the multi-variate function. In other examples, the processing circuitry may modify metrics used in the application of the detection criteria including metrics for evaluating sensor data including data corresponding to physiological parameters. One example metric may be used to determine an accelerator parameter value's contribution to the detection score (e.g., a partial score). In another example mechanism, the processing circuitry of the insertable medical device may modify data (e.g., values) corresponding to the physiological parameters including any of the accelerometer parameter values, the optical sensor parameter values, the temperature parameter value, the bioimpedance parameter value, or the electrogram parameter value mentioned in FIG. 6.

Based on determining that the at least one detection criterion is satisfied, the processing circuitry of the insertable medical device may withhold any output of data indicating the detection of inaccurate sensing, for example, if the processing circuitry sufficiently corrected the sensor data including the data corresponding to the physiological parameters. In some examples, the processing circuitry may halt application of tests predicting medical conditions until the inaccurate sensing is corrected. In some examples, the processing circuitry may continue performing these tests, as part of normal device operation. Until the inaccurate sensing is corrected, the processing circuitry either withhold positive predictions of medical conditions or output data indicative of a confidence level to accompany each positive medical condition prediction. One example confidence level may be the detection score or a modification thereof.

For example, if the insertable medical device is a cardiac monitor, the processing circuitry may determine that a cardiac EGM associated with a suspected asystole episode satisfies a prediction criterion and then, outputs the detection score as the asystole episode prediction's confidence level. In other examples, based on determining that the at least one detection criterion is satisfied, the example operation of FIG. 6 ends. In some examples, based on the example operation of FIG. 6 ending, e.g., due to the at least one detection criterion being satisfied, or an insufficient number or combination of the at least one detection criterion not being satisfied, the processing circuitry may classify the suspected asystole episode as a false asystole episode.

The order and flow of the operation illustrated in FIG. 6 is one example. In other examples according to this disclosure, more or fewer detection criteria may be considered, the detection criteria may be considered in a different order, or satisfaction of different numbers or combinations of detection criteria may be required for a determination that the insertable medical device is inaccurately sensing data including the patient's physiological parameters. Further, in some examples, processing circuitry may perform or not perform the method of FIG. 6, or any of the techniques described herein, as directed by a user, e.g., via external device 12 or computing devices 100. For example, a patient, clinician, or other user may turn on or off functionality for identifying detection criteria remotely (e.g., using Wi-Fi or cellular services) or locally (e.g., using an application provided on a patient's cellular phone or using a medical device programmer).

Figure 7:
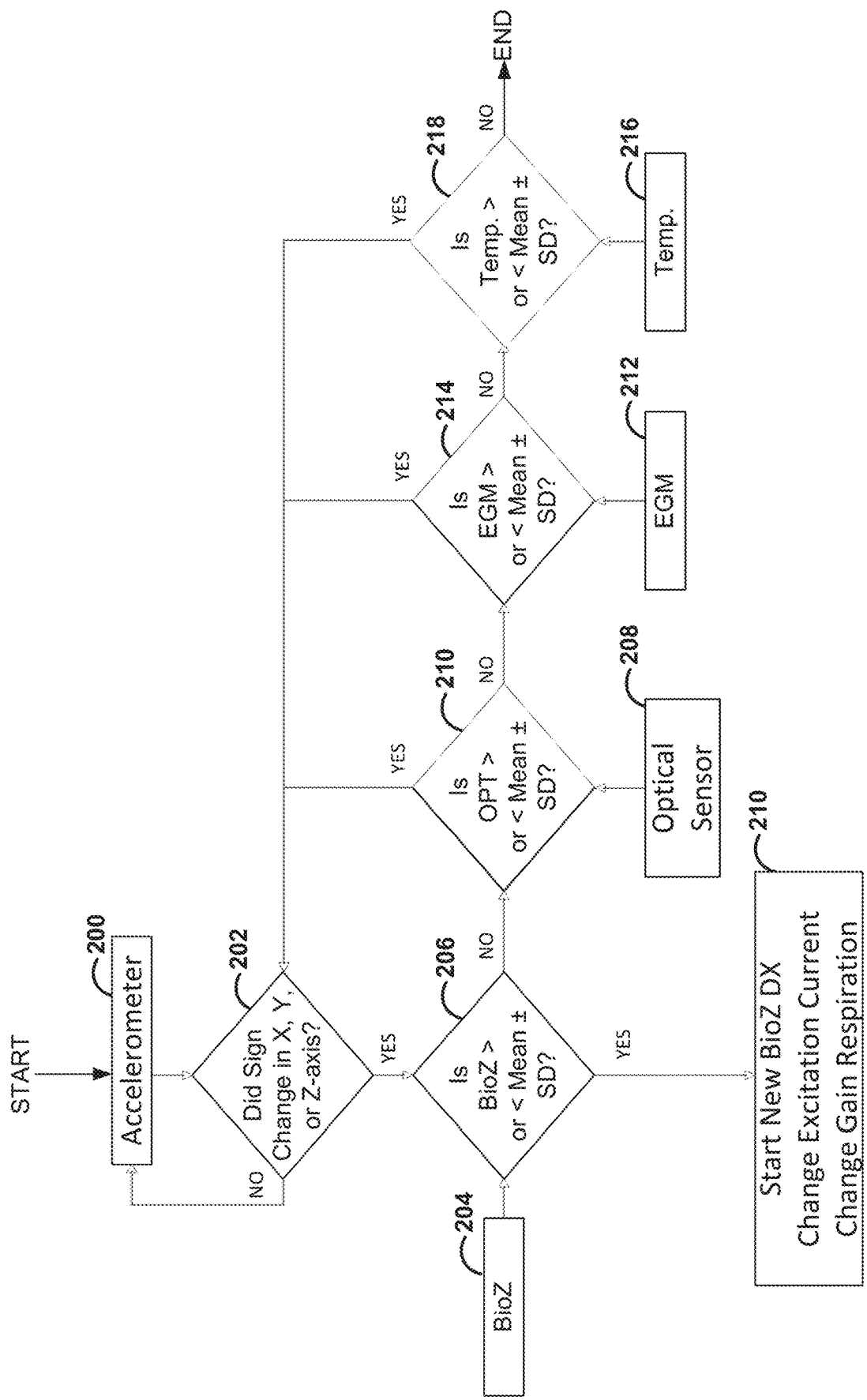
FIG. 7 is a flow diagram illustrating an example operation for detecting an inaccuracy in data corresponding to patient physiological activity that correlates with an incorrect pose.
Figure 8:
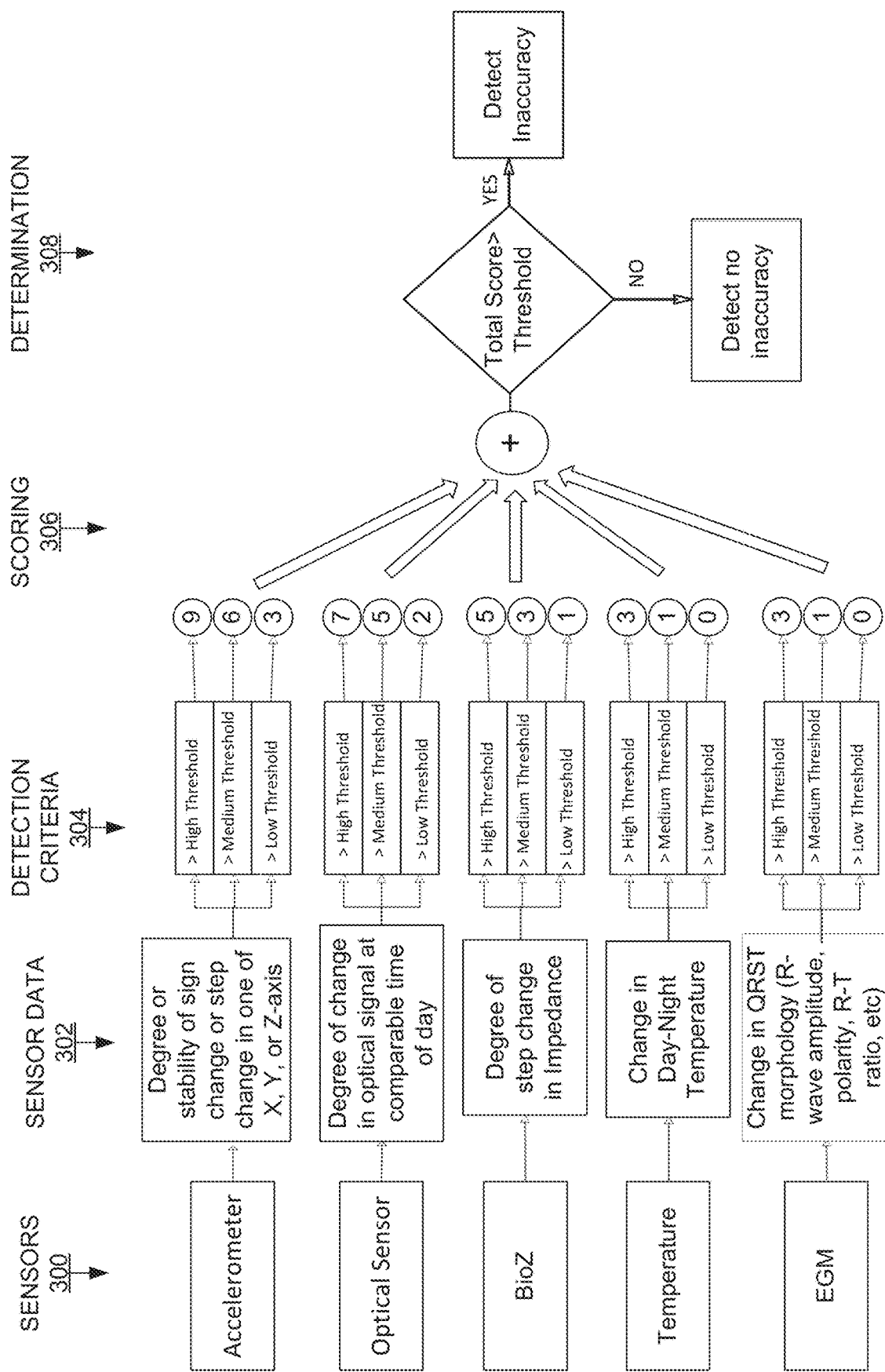
FIG. 8 is a flow diagram illustrating an example operation for comparing data corresponding to patient physiological activity with detection criteria for inaccurate sensing of patient physiological activity.

Additionally, although described in the context of an example in which IMD 10, and processing circuitry 50 of IMD 10, perform each of the portions of the example operation, the example operation of FIG. 6, as well as the example operations described herein with respect to FIGS. 7-8, may be performed by any processing circuitry of any one or more devices of a medical system, e.g., any combination of one or more of processing circuitry 50 of IMD 10, processing circuitry 80 of external device 12, processing circuitry 98 of server 94, or processing circuitry of computing devices 100. In some examples, processing circuitry 50 of IMD 10 may determine whether the at least one detection criterion is satisfied, and provide episode data for the suspected asystole episodes to another device. In such examples, processing circuitry of the other device, e.g., external device 12, server 94, or a computing device 100, may apply the at least one detection criterion to the data corresponding to the patient's physiological parameters.

FIG. 7 is a flow diagram illustrating an example operation for detecting an inaccuracy in data corresponding to patient physiological data that correlates with an incorrect pose. The example operation determines whether any of a plurality of sensor parameter values exceed their respective threshold values, which are each established as a combined value of a mean parameter value and plus or minus one or more standard deviations. Each determination essentially identifies outliers amongst the patient's physiological parameters.

The example operation commences by accessing from accelerometer 200 data including accelerometer parameter values (e.g., movement data, vibration data, and/or the like) and performing determination 202 to determine whether a sign changed in either X-axis, Y-axis, or Z-axis for any accelerometer parameter value. A sign change in any axis most likely results from a device rotation and not from a posture change in the patient body. If determination did 202 determines no sign change, the example operation proceeds to access more data from accelerometer 200 and repeat determination 202 when sufficient accelerometer data is accessed.

If determination 202 produces data indicating a sign change, the example operation of FIG. 7 proceeds to access from a bioimpedance sensor ("bioZ") data including bioimpedance sensor parameter values, e.g., impedance values sensed via electrodes of the sensor device, and perform determination 206 to determine whether any bioimpedance sensor parameter value is greater than or less than a combined value of a mean bioimpedance sensor parameter value plus or minus one or more standard deviations, respectively. In some examples, processing circuitry in performance of determination 206 may determine that each bioimpedance sensor parameter value is within a range between respective combined values of the mean bioimpedance sensor parameter value minus one or more standard deviations and the mean bioimpedance sensor parameter value plus one or more standard deviations. By doing so, determination 206 may detect step changes in the bioimpedance sensor parameter that are not physiological in nature.

If determination 206 produces data indicating at least that at least one bioimpedance sensor parameter value is greater than the first respective combined value or less than the second respective value, example operation proceeds to start a new bioimpedance sensor change expectation current or change gain respiration. In some examples, the processing circuitry of medical system 2, in performance of determination 206, may identify one or more bioimpedance sensor parameter values within a range between the respective combined values and, in response to that identification, may apply any of the above-mentioned mechanisms to modify the bioimpedance sensor parameter values to be exclusive of the range.

If determination 206 produces data indicating that no bioimpedance parameter value is greater than or less than the first or second respective combined values, the example operation proceeds to access data from an optical sensor 208 and perform determination 210 to determine whether an optical sensor parameter is greater than or less than respective combined values of a mean optical sensor parameter value plus or minus one or more standard deviations. If determination 210 produces data indicating that no optical sensor parameter value is greater than the first combined value or less than the second combined value, the example operation proceeds to access data from a cardiac electrogram and perform determination 210 to regarding whether an electrogram parameter value is greater than or less than combined values of the mean electrogram parameter value plus or minus one or more standard deviations, respectively.

If determination 214 produces data indicating that no electrogram parameter value is greater than or less than the respective combined values, the example operation proceeds to access data from a temperature sensor and performed determination 218 to determine whether any temperature parameter value is greater than a first combined value of a mean temperature parameter value plus one or more standard deviations or less than a first combined value of a mean temperature parameter value minus one or more standard deviations. If determination 218 produces data indicating that no temperature parameter value is greater than or less than either combined value, the example operation ends. If either determination 210, determination 214, or determination 218 determine that their respective parameter values are greater than their respective combined value thresholds, the example operation proceeds to repeat determination 202 and/or determination 204. It should be noted that if a particular sensor's input is unavailable, the example operation may skip the corresponding determination where that sensor's input is compared with a threshold.

FIG. 8 is a flow diagram illustrating an example operation for comparing data corresponding to patient physiological activity with detection criteria for inaccurate sensing of patient physiological data.

In general, the example operation of FIG. 8 involves accessing from sensors 300 sensor data 302 including data corresponding to a plurality of physiological parameters as described herein, applying detection criteria 304 certain parameter values, and by scoring 306 those parameter values, determining whether a medical device is currently positioned and/or oriented correctly for accurate sensing (e.g., an incorrect pose).

For sensor data 302, one or more features indicative of a position and/or orientation (i.e., pose) of an insertable medical device within a patient body are determined for each sensor 300. Detection criteria 304 may specify one or more thresholds for each feature and based on comparing the one or more thresholds to that feature, the example operation of FIG. 8 may score that sensor's contribution to a total detection score.

For example, an accelerometer may produce sensor data 302 comprising an accelerometer parameter value indicative of a degree or stability of a sign change or step change in one of X, Y, or Z-axis. As depicted in FIG. 8, the sign or step change (or a confidence level in the step or sign change) may be compared with detection criteria 304 specifying one or more thresholds and based upon which (if any) is/are satisfied, the example operation computes a partial detection score for use in determining whether the insertable medical device is inaccurately sensing the patient's physiological data. FIG. 8 depicts for the accelerometer, three thresholds consisting of a high threshold, a medium threshold, and a low threshold such that scoring 306 assigns a highest score for satisfying the high threshold and a lowest score for only satisfying the low threshold. When the insertable medical device rotates (e.g., flips) and/or migrates, that movement may be directed towards at least one coordinate axis and may be sufficient in magnitude to cross into an opposing half of a cartesian plane, causing a sign change.

As another example, an optical sensor may produce sensor data comprising an optical sensor parameter value indicative a degree of change in optical sensor signal at comparable time(s) of day. As depicted in FIG. 8, an example sample change in optical sensor signal may be compared with detection criteria specifying one or more thresholds and based upon which (if any) in parenthesis is/are satisfied, the example operation computes a second partial detection score for use in determining whether the insertable medical device is inaccurately sensing the patient's physiological data. FIG. 8 depicts for the optical sensor, three thresholds consisting of a high threshold, a medium threshold, and a low threshold such that scoring 306 assigns a highest score for satisfying the high threshold and a lowest score for only satisfying the low threshold. A change in optical sensor signal may indicate a difference in an amount of light being sensed, indicating the insertable medical device rotated and/or migrated to a different portion of the patient's body where the insertable medical device is incapable of accurately sensing the patient's physiological data.

As another example, a bioimpedance may produce sensor data 302 comprising a bioimpedance parameter value indicative of a degree of a step change in impedance over a period of time. As depicted in FIG. 8, the step change may be compared with detection criteria specifying one or more thresholds and based upon which (if any) is/are satisfied, the example operation computes a third partial detection score for use in determining whether the insertable medical device is inaccurately sensing the patient's physiological data. Similar to the accelerometer and the optical sensor, FIG. 8 depicts for the bioimpedance three thresholds consisting of a high threshold, a medium threshold, and a low threshold such that scoring 306 assigns a highest score for satisfying the high threshold and a lowest score for only satisfying the low threshold. Different types of tissue within the patient's body may vary in electrical impedance and, as demonstrated herein, determining which tissue is proximate to electrodes of the insertable medical device may be based upon the impedance associated with the tissue. If the proximate tissue is not conducive for accurate sensing, the insertable medical device most likely is in an incorrect pose for sensing and/or in a portion of the patient's body that is unsuitable for accurate sensing.

As yet another example, a temperature sensor may produce sensor data 302 comprising a temperature parameter value indicative of a change in day-night temperature. As depicted in FIG. 8, the temperature change may be compared with detection criteria specifying one or more thresholds and based upon which (if any) is/are satisfied, the example operation computes a fourth partial detection score for use in determining whether the insertable medical device is inaccurately sensing the patient's physiological data. Similar to the accelerometer, the optical sensor, and the bioimpedance sensor, FIG. 8 depicts for the temperature sensor three thresholds consisting of a high threshold, a medium threshold, and a low threshold. If the day-night temperature difference fluctuates, the insertable medical device most likely migrated and/or rotated into an incorrect pose for sensing and/or to a portion of the patient's body that is unsuitable for accurate sensing.

As yet another example, an electrogram sensor may produce sensor data 302 comprising an electrogram parameter value indicative of a change in QRST morphology (R-wave amplitude, polarity, R-T ratio, and/or the like). As depicted in FIG. 8, the temperature change may be compared with detection criteria specifying one or more thresholds and based upon which (if any) is/are satisfied, the example operation computes a fifty partial detection score for use in determining whether the insertable medical device is inaccurately sensing the patient's physiological data. Similar to other ones of sensors 300, FIG. 8 depicts for the electrogram sensor three thresholds consisting of a high threshold, a medium threshold, and a low threshold. If the change in QRST morphology is excessive, the insertable medical device most likely is in an incorrect pose for sensing and/or to a portion of the patient's body that is unsuitable for accurate sensing.

After comparing parameter values of sensor data 302 with thresholds of detection criteria 304, scoring 306 computes each partial detection score followed by computing a summation of the partial detection score into a total detection score based upon all of sensors 300. The example operation of FIG. 8 concludes with determination 308 in which the total detection score is compared with a total score threshold specified by the detection criteria. Based on determining that the total detection score satisfies the total score threshold (YES of 308), the example operation of FIG. 8 positively detects an inaccuracy in the sensing of one or more patient physiological parameters by the insertable medical device.

Based on determining that the total detection score does not satisfy the total score threshold (NO of 308), the example operation of FIG. 8 does not detect any inaccuracy in the sensing of any patient physiological parameter by the insertable medical device.

It should be noted that examples of detection criteria are determined based on an analysis of training data from a population of patients including feedback identifying false determinations. Each threshold and score may be assigned to parameter values is learned through training with sensors 300 sensing physiological data of a number of patients over a sufficient time period. A threshold and score may be fine-tuned (e.g., back-propagation) over time, especially in view of false positives and false negatives.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical system comprising:
    sensory sub-system comprising:
        one or more sensors, each of the one or more sensors configured to capture a signal indicating one or more patient physiological parameters, the one or more sensors comprising at least one electrode configured to sense an impedance of a portion of the patient body proximate to the electrode; and
        sensing circuitry coupled to the one or more sensors and configured to generate data corresponding to the one or more patient physiological parameters; and
    processing circuitry configured to:
        detect an inaccuracy in the data corresponding to the one or more patient physiological parameters based upon data including at least the sensed impedance of the portion of the patient body, wherein to detect the inaccuracy the processing circuitry is further configured to compute a detection score for determining whether the one or more sensors at least one of migrated or rotated based on comparing the data corresponding to the one or more physiological parameters with respective detection criteria for at least one of the migration or the rotation of the one or more sensors;
        correct at least a portion of the inaccuracy in the data corresponding to the one or more patient physiological parameters by modifying at least one of:
            a first detection criterion wherein the first detection criterion is a part of the computation of a detection score, and
            a second detection criterion wherein second detection criterion comprises a threshold value for the comparison with a patient physiological parameter value or with the detection score; and
        generate, for display on a display device, output data indicating the inaccuracy in the data corresponding to the one or more patient physiological parameters.

2. The medical system of claim 1, wherein to detect the inaccuracy in the data corresponding to the one or more patient physiological parameters based upon the sensed impedance of the proximate portion of the patient body,
    the processing circuitry is further configured to determine the at least one of the migration or the rotation of the one or more sensors based upon the impedance of the portion of the patient body.

3. The medical system of claim 1, wherein the processing circuitry is configured to detect the inaccuracy in the data corresponding to the one or more patient physiological parameters based upon the sensed impedance of the proximate portion of the patient body,
    wherein the processing circuitry is further configured to detect, based upon the impedance of the portion of the patient body, that the portion of the patient body differs from a pre-determined portion of the patient body.

4. The medical system of claim 1, wherein the one or more sensors further comprise one or more of an accelerometer, an optical sensor, or a temperature sensor, wherein the processing circuitry is configured to detect the inaccuracy in the data corresponding to the one or more patient physiological parameters based upon data from the one or more of the accelerometer, the optical sensor, or the temperature sensor.

5. The medical system of claim 1, wherein the at least one electrode is further configured to sense a cardiac electrogram of the patient, wherein the processing circuitry is configured to detect the inaccuracy in the data corresponding to the one or more patient physiological parameters based upon data from the cardiac electrogram.

6. The medical system of claim 1, wherein the processing circuitry is configured to determine that a pose of the one or more sensors within the patient body differs from a pre-determined pose within the patient body based upon the data corresponding to the one or more patient physiological parameters including sensor data from two or more of an accelerometer, an optical sensor, an temperature sensor, or a bioimpedance sensor, the inaccuracy correlating with a simultaneous change in the respective sensor data of each sensor.

7. The medical system of claim 1,
wherein the processing circuitry is further configured to determine that a pose of the one or more sensors within the patient body deviates from a pre-determined pose within the patient body based upon the data corresponding to the one or more patient physiological parameters including the sensed impedance of the portion of the patient body, the inaccuracy correlating with the deviation from the pre-determined pose, the pre-determined pose corresponding to an intended insertion of the one or more sensors into the patient body.

8. The medical system of claim 1, wherein the processing circuitry is configured to communicate the detection score to a remote computer as a confidence level for a medical condition alert for the patient.

9. The medical system of claim 1, wherein the processing circuitry is configured to withhold, from the output to the display device, a medical condition alert for the patient based upon the detection score.

10. The medical system of claim 1, wherein the processing circuitry is configured to invalidate the data corresponding to the one or more patient physiological parameters if the correction is unsuccessful at correcting the at least a portion of the inaccuracy in the data corresponding to the one or more patient physiological parameters.

11. The medical system of claim 10, wherein the processing circuitry is configured to reject a medical condition prediction rendered by a medical device when, for that prediction, the medical device uses, at least in part, the data corresponding to the one or more patient physiological parameters.

12. The medical system of claim 10, wherein the processing circuitry is configured to withhold display, storage, or communication of the data corresponding to the one or more patient physiological parameters.

* * * * *